(12) United States Patent
Kannan et al.

(10) Patent No.: US 6,300,502 B1
(45) Date of Patent: Oct. 9, 2001

(54) MULTI-ARMED CHROMOPHORES WITH VERY LARGE TWO-PHOTON ABSORPTION CROSS-SECTIONS

(75) Inventors: Ramamurthi Kannan, Cincinnati, OH (US); Bruce A. Reinhardt, deceased, late of Las Vegas, NV (US), Erin D. Reinhardt and Jason A. Reinhardt, administrators; Loon-Seng Tan, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/731,549

(22) Filed: Dec. 8, 2000

(51) Int. Cl.$^7$ .................................................. C07D 277/66
(52) U.S. Cl. ........................................... 548/156; 548/160
(58) Field of Search ...................................... 548/156, 160

(56) References Cited

U.S. PATENT DOCUMENTS

| | | | |
|---|---|---|---|
| 5,770,737 | 6/1998 | Reinhardt et al. | 546/285 |
| 5,859,251 | 1/1999 | Reinhardt et al. | 546/255 |
| 6,100,405 | 8/2000 | Reinhardt et al | 548/160 |

OTHER PUBLICATIONS

S.M. Kirkpatrick, J.W. Baur, C.M. Clark, L.R. Denny, D.W. Tomlin, B.R. Reinhardt, R. Kannan, M.O. Stone, Holographic recording using two–photon–induced photopolymerization, Appl. Phys. A 69, 461–464 (1999) Published online: Sep. 8, 1999.

G.S. He, J. Swiatkiewicz, Y. Jiang, P.N. Prasad, B.A. Reinhardt, L–S Tan, R. Kannan, Two–Photon Excitation and Optical Spatial–Profile Reshaping via a Nonlinear Absorbing Medium, J. Phys. Chem. A 2000, 104, 4805–4810. Published on web May 25, 2000.

*Primary Examiner*—Laura L. Stockton
(74) *Attorney, Agent, or Firm*—Charles E. Bricker; Thomas L. Kundert

(57) ABSTRACT

Provided are chromophores with very large two-photon absorption cross-sections. One group of these chromophores has the formula:

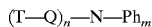

wherein Q is a single bond or 1,4-phenylene, Ph is a phenyl group, n has a value of 1–3 and m has a value of 3–n, and wherein T is

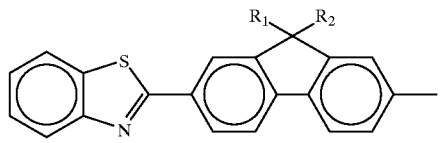

wherein $R_1$ and $R_2$ are alkyl groups having 1 to 20 carbon atoms, provided that when Q is a single bond, the value of n is 2 or 3.

Another group of these chromophores has the formula:

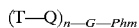

wherein T is as defined above, Q is a single bond or 1,4-phenylene, Ph is a phenyl group, n has a value of 1–4 and m has a value of 4–n, and wherein G is a 4-arm core unit.

Yet another group of these chromophores has the formula:

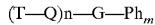

wherein T is as described previously, Q is a single bond or 1,4-phenylene, Ph is a phenyl group, n has a value of 1–6 and m has a value of 6–n, and wherein G is a 6-arm core unit.

9 Claims, No Drawings

MULTI-ARMED CHROMOPHORES WITH VERY LARGE TWO-PHOTON ABSORPTION CROSS-SECTIONS

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with very large two-photon absorption cross-sections.

The two-photon process, predicted theoretically in 1931 and observed experimentally in the 1960s, has received little consideration for practical application. The lack of the availability of dyes with sufficiently large cross-sections has made many practical applications appear unattainable. Recently, the synthesis of new dyes with increased cross-sections and large upconverted fluorescence has opened up a myriad of new applications. These new applications include two-photon upconverted lasing, two-photon optical power limiting, three-dimensional optical data storage, and photodynamic therapy. Another application which has, unlike the others, received a reasonable amount of attention is three-dimensional imaging using two-photon laser scanning confocal microscopy. Multi-photon microscopy appears to be of great value as an imaging technique for numerous biological systems as well as organic paints and coatings. This technique, like the others, has never reached its full potential due to the lack of dyes which exhibit high intensity upconverted fluorescence. A tremendous improvement in the depth of confocal microscopic imaging can be obtained when the two-photon peak occurs at or near 800 nm, a wavelength at which most organic and biological materials have large optical transparency. It follows that a major molecular design challenge is to increase the molecular two-photon cross-section without shifting the two-photon absorption peak away from 800 nm. The U. S. Air Force currently has a strong interest in the development of two-photon technology as both an imaging tool for the nondestructive evaluation (NDE) of aircraft paint and as a useful material for optical power limiting. It is evident that in order for two-photon technology to realize its full potential, major improvements will be necessary in the design and synthesis of more active dye molecules with the necessary solubility and photo-stability.

The probability of absorption of two long wavelength photons from the laser source simultaneously is dependent upon the two-photon cross-section of the dye molecule. In U.S. Pat. No. 5,770,737, Reinhardt et al, issued Jun. 23, 1998, there are described asymmetrical fluorene-containing two-photon chromophores of the formula:

D—Ar—A wherein the Ar core is

or

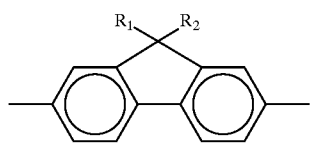

-continued

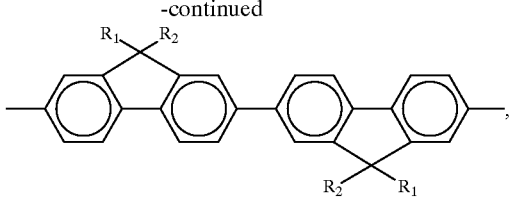

wherein $R_1$ and $R_2$ are alkyl groups having 8 to 12 carbon atoms, and wherein $R_1$ and $R_2$ are the same or different, wherein D is an electron donor moiety selected from the group consisting of

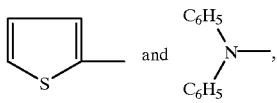

and wherein A is an electron acceptor moiety selected from the group consisting of

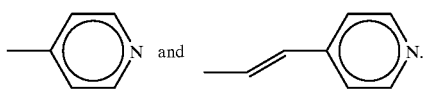

The most active dyes described in U.S. Pat. No. 5,770,737 incorporate an easily polarizable olefinic double bond in the backbone of the molecule. This olefinic bond, although greatly increasing the two-photon absorption (TPA) cross-section of chromophores, has limited thermal and photochemical stability, thus reducing the range of its utility.

In U.S. Pat. No. 6,100,405, issued Aug. 8, 2000, to Reinhardt et al there are disclosed dyes with increased thermal and photochemical stability while maintaining the same level of two-photon activity. These asymmetrical two-photon chromophores have the formula:

D—Ar—A wherein Ar is selected from the group consisting of

—Fl—, —Fl—$C_6H_4$—, —Fl—Fl—, and —Fl—Fl—Fl—, wherein Fl is a fluorene group of the formula:

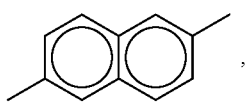

wherein $R_1$ and $R_2$ are alkyl groups having 2 to 20 carbon atoms, and wherein $R_1$ and $R_2$ are the same or different;

wherein D is

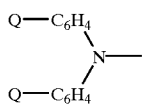

wherein Q is selected from the group consisting of —H, —OH and —O—$C_xH_{2x+1}$, wherein x has a value of 1 to 10;

and wherein A is selected from the group consisting of

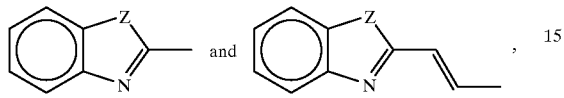

wherein Z is selected from the group consisting of —O— and —S—.

Accordingly, it is an object of the present invention to provide more active dye molecules with the necessary solubility and photo-stability.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided multi-armed chromophores with very large two-photon absorption cross-sections. One group of these chromophores have the formula:

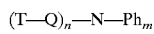

wherein Q is a single bond or 1,4-phenylene, Ph is a phenyl group, n has a value of 1–3 and m has a value of 3-n, and wherein T is

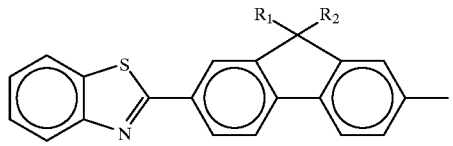

wherein $R_1$ and $R_2$ are alkyl groups having 1 to 20 carbon atoms, provided that when Q is a single bond, the value of n is 2 or 3. Preparation of these chromophores is described in the Examples which follow.

Another group of these chromophores have the formula:

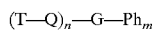

wherein T is as defined above, Q is a single bond or 1,4-phenylene, Ph is a phenyl group, n has a value of 1–4 and m has a value of 4-n, and wherein G is a core unit selected from the group consisting of

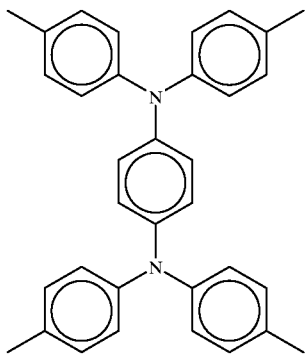

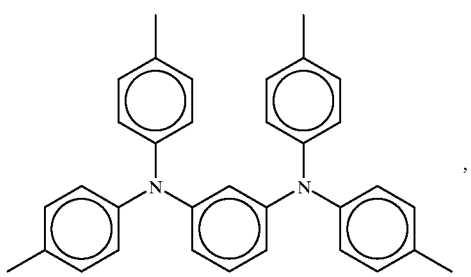

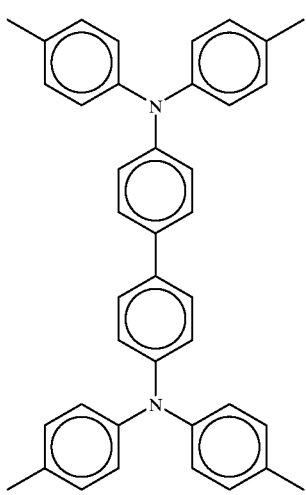

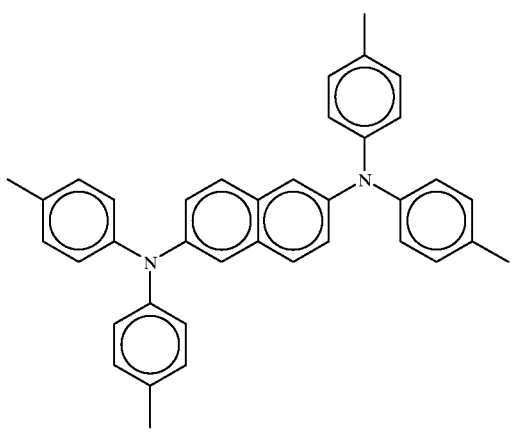

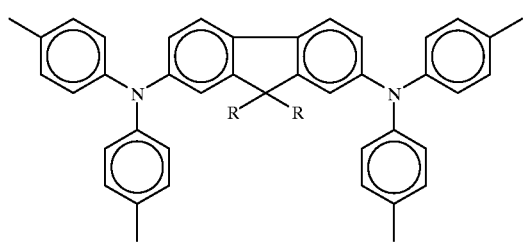

and

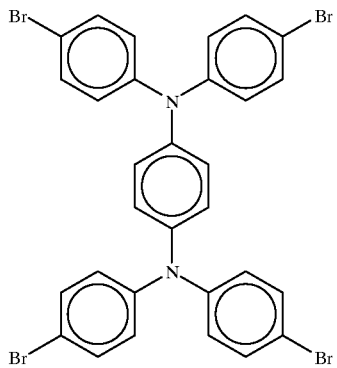

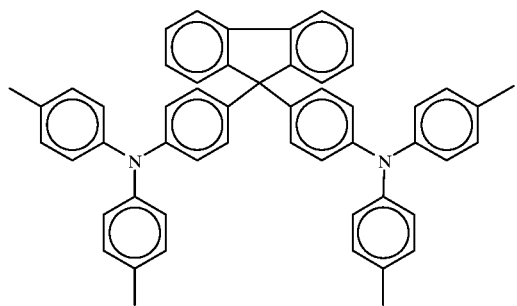

Yet another group of these chromophores have the formula:

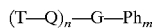

$(T-Q)_n-G-Ph_m$ wherein T is as described previously, Q is a single bond or 1,4-phenylene, Ph is a phenyl group, n has a value of 1–6 and m has a value of 6−n, and wherein G is a core unit having the structure

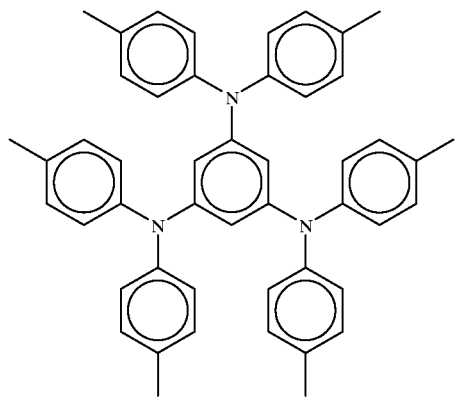

The 4-and 6-arm chromophore cores can be synthesized from their respective polybromo compounds following the procedures given in the following Examples. The polybromo cores (G) can be synthesized using a modified Ullmann reaction or palladium-catalyzed amination. For example, the polybromo core can be synthesized from 1,4-phenylenediamine and 1-bromo-4-iodophenylene. The other cores can be synthesized using polyamines including, but not limited to 1,3-phenylenediamine, benzidine, 2,7-diaminofluorene, 2,6-diaminonaphthalene, 1,3,5-triaminobenzene, and 9,9-bis(4-aminophenyl)fluorene.

The following Examples illustrate the invention:

EXAMPLE 1

2,7-Dibromofluorene

To a mechanically stirred mixture of fluorene (113.76 g., 0.68 moles), iodine (1.96 g., 0.0077 moles), and methylene chloride (750 ml), bromine (74 ml, 1.44 moles) diluted with methylene chloride (100 ml) was added dropwise at room temperature over a period of 1.5 hours. After 5 minutes, a solution of sodium bisulfite (15.0 g.) in water (100 ml) was added and the mixture was stirred for 30 minutes, when the mixture became colorless. Water (750 ml) was then added, and methylene chloride was distilled off. The product slurry was filtered and the product was air-dried, 220.5 g., m.p. 151 (shrank), 156–160° C. This material was used in the next step without further purification.

EXAMPLE 2

9,9-Diethyl-2,7-Dibromofluorene

To a mechanically stirred mixture of 2,7-dibromofluorene (66.5 g., 0.205 mol.) (commercially available), powdered potassium hydroxide (56.0 g., 1.0 mol.), potassium iodide (3.4 g.) and DMSO (150 ml), cooled to 10° C., ethyl bromide (40 ml, 58.4 g. 0.536 mol.) was added dropwise over 45 minutes. The mixture turned from red to light purple. After allowing the temperature to warm to 20° C., the mixture was left overnight to stir and poured into water, 77.0 g.(98.7% yield), m.p. 144–153° C. The product was then recrystallized from hexane (550 ml) with charcoal treatment, and collected in two crops, m.p. 154–157° C. and 153–154° C., totalling 60.36 g. (77.4% yield).

EXAMPLE 3

9,9-Diethyl-7-bromo-fluorene-2-carboxaldehyde

To a mechanically stirred solution of 9,9-diethyl-2,7-dibromofluorene (59.38 g., 0.1563 mol.), in THF (325 ml), cooled in dry ice-ethanol bath, n-butyl lithium (104 ml of 1.6M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 ml of concentrated hydrochloric acid diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane -ethyl acetate (9:1), to get colorless solids, 40.29 g. (78.4% yield) m.p. 126–128° C. The mother liquor after chromatography over 150 g. silicagel, elution with 1:1 heptane-toluene, and trituration of residual solids in hexanes gave additional product, 6.56 g. (12.8% yield, total 91% yield), m.p. 126–128° C. Mass Spec: (m/z) 328,330, (M+). A sample for analysis was prepared by recrystallization from hexanes, m.p. 127–129° C. Anal: Calcd for $C_{18}H_{17}BrO$: C, 65.55; H, 5.20; and Br, 24.27. Found: C, 65.60; H, 5.51; and Br, 24.71.

EXAMPLE 4

2-(9,9-diethyl-7-bromo-2-) fluorenyl benzothiazole

A mixture of 9,9-Diethyl-7-bromo-fluorene-2-carboxaldehyde (49.35 g., 0.15 mol.), 2-amino thiophenol (20 ml. 0.187 mol., 1,25 eq.), and DMSO (110 ml) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the product benzothiazole, 45.69 g., m.p. 133.6–135° C. An additional 6.6 g., m.p. 134.6–135.5° C., was obtained by chromatography of the ethanol filtrate. Total recovery 52.29 g. (80.3% yield). Mass Spec: m/z 433, 435, (M+). Anal: Calcd for $C_{24}H_{20}BrNS$: C, 66.37; H, 4.64; Br, 18.40; N, 3.23; and S, 7.37. Found: C, 66.46; H, 4.52; Br, 18.54; N, 3.14; and S, 7.19.

EXAMPLE 5

4-Bromotriphenylamine

A mixture of 1-bromo-4-iodobenzene (11.30 g., 40 mmol.), diphenylamine (6.65 g., 39.3 mmol.), powdered potassium carbonate (26.6 g., 192.7 mmol.), 18-crown-6 (1.06 g., 4 mmol.), copper bronze (1.37 g., 21.6 mmol.), and 1.2-dichlorobenzene (40 ml) was kept at 190° C., cooled and filtered. The residue left on concentration of filtrate, was chromatograhped on silica gel. After elution with hexanes (1 liter), the product came out in 9:1 toluene hexanes eluates, and was isolated as a colorless solid after trituration with methanol, 4.47 g. (35% yield), m.p. 113–115° C. Mass Spec (m/z): 371 (M+iodotriphenylamine), 323 325 (M+).

EXAMPLE 6

(4-(7-benzothiazol-2-yl-9,9-diethylfluoren-2-yl) phenyl)diphenylamine

To a solution of bromotriphenylamine (8.1 g., 0.025 mol.) in THF (125 ml) cooled to below −50° C., a solution of n-butyl lithium in hexanes (18 ml., 0.0288 mol., 1.152 eq.) was added and stirred for 30 minutes. A solution of tributyl tin chloride (8.5 ml, 0.0313 mol.) in THF was added, the mixture was kept in the cooling bath for 1 hour, and then allowed to warm to room temperature. After cooling in an ice bath, a solution of potassium fluoride was added, stirred for 1 hour, diluted with 100 ml of toluene, the organic phase was dried and concentrated to leave 16.3 g. oil. Mass Spec: (m/z) 531, 533, 535, (M+, organotin). This oil was dissolved in toluene (100 ml), mixed with 2-(9,9-diethyl-7-bromo-2-) fluorenyl benzothiazole, (9.0 g., 0.0207 mol.) and bistriphenyl phosphino palladium (II) chloride (0.9 g., 0.0013 mol.) and held at 95–100° C. for 18 hours. After cooling, the mixture was treated with a solution of potassium fluoride, stirred one hour, and the insoluble fluoride (9.19 g.) was filtered off. The filtrate was concentrated, and the residue was transferred to a column of silica gel. Elution with heptane removed 1.43 g. (18%) yield), m.p. 95–97° C. of a material identified as diphenylamino biphenyl; Mass Spec: m/z 321 (M+). Elution with toluene:heptane 1:4 gave 0.35 g., m.p. 185–1950° C., identified as tetraphenyl benzidine; Mass Spec: (m/z) 488 (M+). The desired product was obtained on elution with toluene:heptane 1:1, followed by recrystallization from the same solvent, 7.66 g. (64% yield), m.p. 205.5–208° C. Mass Spec: (m/z) 598, (M+), 569 (M-$C_2H_5$), 554 (M-$CH_3$). Anal: Calcd for $C_{42}H_{34}N_2S$: C, 84.25; H, 5.72; N, 4.68; and S, 5.34. Found, C, 84.52; H, 5.54; N, 4.48 and S, 5.35.

EXAMPLE 7

4,4'-Dibromo-4"-(9,9-diethyl-7-(2-benzothiazolyl)-2-fluorenyl triphenylamine

To a slurry of (4-(7-benzothiazol-2-yl-9,9-diethylfluoren-2-yl) phenyl)diphenylamine (6.0 g., 0.010 mole), in DMF (150 ml), cooled in ice-water bath, N-bromosuccinimide (3.56 g., 0.020 mole),was added, and the mixture was stirred for 18 hours to get a green solution. The solids that separated on dilution with water, was transferred to a column of 225 g., alumina, the column was eluted with 1:1 toluene-heptane, to get the product. The product was recrystallized from 1:1 toluene-heptane, 7.05 g., m.p. 214–217° C. (93% yield). Further recrystallizations raised the m.p. to 216.4–218.8° C. Anal: Calcd for $C_{42}H_{32}N_2Br_2S$: C, 66.67; H, 4.26; N, 3.70; Br, 21.12; and S, 4.23. Found: C, 66.79; H, 4.38; N, 3.50; Br, 21.33; and S, 3.94.

EXAMPLE 8

7-(2-Benzothiazolyl)-9,9-diethylfluorene-2-boronic acid

To a solution of 2-(9,9-diethyl-7-bromo-2-) fluorenyl benzothiazole, (19.5 g., 0.045 mole), in THF (240 ml), cooled in a dryice-acetone bath, a solution of n-butyl lithium in hexanes (33 ml, 0.0528 mole 1.173 eq.) was added dropwise, and after 25 minutes, tri-isopropyl borate (27 ml,0.117 mole), was syringed in. After 3 hours, the cooling bath was removed, and on warming to 5° C., the brown slurry turned into a green solution, and at 20° C. (in 1 hour), a brown solution resulted. This was cooled to 5° C., and treated with a mixture of 15 ml, concentrated hydrochloric acid and 25 ml water. The THF layer was separated, and the aqueous layer was extracted with 200 ml ether. The combined organic phase was concentrated, the residual solids were suspended in toluene, filtered, and washed with toluene, 17.0 g., m.p. 160–163° C. (ca 100% yield).

EXAMPLE 9

Bis(4-(7-benzothiazol-2-yl-9,9-diethylfluoren-2-yl) phenyl)phenylamine 4,4'-dibromotriphenylamine: To a magnetically stirred solution of diphenylamine (17.0 g., 0.1 mol.), in dimethylformamide (100 ml), at 10° C., N-bromosuccinimide (35.5 g., 0.2 moles) was added in portions, keeping temperature below 20° C. The mixture was stirred at room temperature for 18 hours and then poured into 1000 ml of water. The oil that first separated, solidified on stirring to leave 32 g., of solids. Recrystallization from hexanes gave 4,4'-dibromodiphenylamine, m.p. 105–107° C., 18,8 g., 60% yield. The same dibromo compound can also be obtained in near quantitative yields, by reacting diphenylamine (2.65 g.) with 48% hydrobromic acid (10 ml) in DMSO (15 ml). Mass Spec (mlz): 325, 327, 329 (M+).

4,4'-dibromotriphenylamine: A mixture of 4,4'-dibromodiphenylamine (7.3 g. 22 mmol), cyclohexane-1,4-dione (2.5 g., 23.3 mole), para-toluenesulfonic acid (0.1 g.) and toluene (100 ml) was kept at reflux with a Dean-Stark phase separator containing 4A molecular sieves. After 18 hours at reflux, the reaction was diluted with toluene, and the toluene solution was washed with water, dried and concentrated. The residue was dissolved in hexanes, and the hexanes solution was passed through a column of silica gel to afford 4,4'-dibromotriphenylamine as a colorless glass, 5.04 g., 67% yield. Mass Spec (m/z): 401, 403, 405 (M+).

Bis(4-(7-benzothiazol-2-yl-9,9-diethylfluoren-2-yl)phenyl)phenylamine: A mixture of 4,4'-dibromotriphenylamine (2.06 g., 5 mmol.), 9,9-diethyl-7-(2-benzothiazolyl)-2-fluorene boronic acid (6.24 g., 15.6 mmol.), ethanol (40 ml), and N-methyl-2-pyrrolidinone (100 ml) was heated under nitrogen to 120° C., and cooled. To the mixture, sodium carbonate (5.2 g., 50 mmol.) and 5% palladium on carbon (1.6 g.) were added and the reaction mixture was kept at 110° C. for 42 hours. The cooled reaction mixture was poured into 750 ml water, and the separated green solids containing the chromophore were collected. These were transferred to a column of alumina and eluted with heptane to obtain 2.65 g., 56% yield of the product, m.p. 256.7–261.9° C. Recrystallization from toluene-heptane (3:1) raised the m.p. to 259.6–263° C. Mass spec (m/z): 951 (M+). Anal. Calcd. for $C_{66}H_{53}N_3S_2$: C, 83.25; H, 5.61; N, 4.41; S, 6.72. Found: C, 83.10; H, 5.35; N, 4.24; S, 6.50.

EXAMPLE 10

N,N,N-tri(4-(7-benzothiazol-2-yl-9,9-diethylfluoren-2-yl)phenyl)amine

A mixture of 4,4'-dibromo-4"-(9,9-diethyl-7-(2-benzothiazolyl)-2-fluorenyl triphenylamine (1.9 g., 2.5 mmol), benzothiazolyl fluorenyl boronic acid, (2.75 g.,~6.9 mmol), palladium on carbon (5%, unreduced, 0.62 g.), ethanol (20ml), N-methyl-2-pyrrolidinone (60 ml), and sodium carbonate (2.34 g., 22 mmol), was stirred in an oil bath maintained at 100° C. for 20 hours, cooled and filtered. The filtrate was diluted with water to get the crude product, 4.9 g. This was transferred to an alumina column (200 g). After elution with 1:1 toluene-heptane, the column was eluted with toluene to get the desired product, which was suspended in methanol and collected; 2.06 g., (63% yield), m.p. 338–341.40° C. Recrystallizations from toluene-heptane raised the m.p. to 349.1–352.00° C. Anal: Calcd for $C_{90}H_{72}N_4S_3$: C, 82.80; H, 5.56; N, 4.29 and S, 7.35. Found: C, 82.89; H, 5.39; N, 4.01; and S, 6.88.

EXAMPLE 11

(7-Benzothiazol-2-yl-9,9-diethylfluoren-2-yl)diphenylamine

A mixture of 2-(9,9-diethyl-7-bromo-2-) fluorenyl benzothiazole, (6.6 g., 0.015 mol.), potassium carbonate (10.3 g.,0.0746 mol.), diphenylamine (4.5 g. 0.0376 mol.), potassium iodide (9.6 g. 0.0173 mol.), copper bronze (2.0 g., 0.0317 mol.), copper (I) iodide (1.5 g., 0.0079 mol.), 18-crown-6 (0.96 g., 0.0036 mol.), and 1,2-dichlorobenzene (45 ml.) was kept at 180–1820° C. for 20 hours, cooled and filtered. The filtrate was concentrated and the residue was transferred to a column of silica gel. Elution with heptane gave the product, 3.6 g.(45.5% yield), m.p. 175–178.4° C. Recrystallization from 9:1 heptane-toluene raised the m.p. to 178–180° C. Mass Spec: (m/z) 522, (M+). Anal. Calcd. for $C_{36}H_{30}N_2S$: C, 82.76; H, 5.79; N, 5.36; and S, 6.12. Found: C, 82.41; H, 5.52; N, 5.25; and S, 5.99.

EXAMPLE 12

N,N-Bis(7-benzothiazol-2-yl-9,9-diethylfluoren-2-yl)phenylamine

To a 100 ml three-necked, round-bottomed flask fitted with a reflux condenser, a Dean-Stark trap, an $N_2$ inlet-outlet and a stir bar the following was added: 2-(7-bromo-9,9-diethylfluorene-2-yl)benzothiazole, (8.68 g, 0.02 mol), toluene (65 ml), and aniline (0.01 mol, 0.91 ml). The flask contents were heated to reflux in an oil bath. Approximately 25 ml of toluene was azeotroped over into a Dean-Stark trap. The flask is cooled slightly and bis(dibenzylideneacetone) palladium(0) (0.22 g, 0.00038 mol), 1,1-bis (diphenylphosphine)ferrocene (0.21 g, 0.00038 mol.), and sodium-t-butoxide (2.94 g, 0.03 mol.) were added. The flask was heated to 90° C. overnight. The reaction mixture was allowed to cool to room temperature under nitrogen and an additional 10% of 2-(7-bromo-9, 9-diethylfluorene-2-yl) benzothiazole, 4 (0.868 g, 0.002 mol) was added. The reaction mixture was then heat to 105° C. and kept at that temperature for four hours. The reaction was then cooled to room temperature. The precipitated solid was collected by filtration. The crude product was subsequently recrystallized twice from toluene and dried under vacuum at 100° C. overnight. This resulted in 80% yield with a m.p. 299.7–302.1° C. Anal. Calcd. for $C_{54}H_{45}N_3S_2$: C, 81.06; H, 5.66; N, 5.25; S, 8.01. Found: C, 80.74; H, 5.59; N, 5.13; S, 7.62. Mass spec. (m/z) 799 (M+).

EXAMPLE 13

9,9-Diethyl-7-iodofluorene-2-carboxaldehyde

A mixture of 9,9-diethyl-7-bromofluorene-2-carboxaldehyde, (28.8 g., 0.0875 mol.), nickel (II) bromide (2.1 g., 9.6 mmol.), tri-n-butyl phosphine (4m1, 16 mmol.), potassium iodide (52.0 g., 0.3132 mole, 3.6 equivalents), and DMF (125 ml), was held at reflux under an atmosphere of nitrogen for 15 hours, cooled, diluted with toluene (450 ml), and filtered. The filtrate was washed with water in several portions, dried, and concentrated. The residual solids were recrystallized from toluene-heptane (1:2, 150 ml); 24.79 g., m.p. 138–140° C., (75% yield). When the reaction was run longer, 24 and 34 hours, the yields fell to 61 and 59% respectively. Mass Spec (m/z): 376 (M+), not contaminated with the bromo aldehyde. Anal.Calcd. for $C_{18}H_{17}OI$: C, 57.46; H, 4.55; and l, 33.73%. Found: C, 58.04 and 58.02; H, 4.72 and 4.66; and l, 32.62 and 32.89.

EXAMPLE 14

9,9-Diethyl-7-(2-benzothiazolyl)-2-iodofluorene

A mixture of iodofluorene aldehyde, (17.2 g., 0.046mol.), 2-aminothiophenol (5 ml, 5.85 g., 0.0467 mole) and DMSO (40 ml) was kept in an oil-bath held at 185–190° C. for 45 min, cooled, and poured into a solution of sodium chloride. The precipitated solids were collected, and recrystallized from toluene-heptane, after treatment with charcoal and clarification. 13.61 g., (62%), m.p. 158–160° C. Additional 3.65 g. (16%) m.p. 160–161.5° C. was isolated from chromatography of the recrystallization mother liquors. Total yield was 78%. Two recrystallizations from ethyl acetate-heptane raised the m.p. to 162–164° C. Mass Spec: (m/z) 481 (M+). Anal. Calcd. for $C_{24}H_{20}NSl$: C, 59.88; H, 4.19; N, 2.91; S, 6.66; 1, 26.36. Found: C, 60.27; H, 4.41; N, 3.02; S, 6.69; 1, 26.35.

EXAMPLE 15

9,9-Diethylfluorene

To a mechanically stirred mixture of fluorene (83.2 g. 0.5 mol.), powdered potassium hydroxide (140 g., 2.5 mol.), potassium iodide (4.0 g., 0.024 mol.) and DMSO (225 ml), cooled to 15–20° C., bromoethane (104 ml., 151.84 g., 1.39 mol.) was added over a period of 1.5 hours, and allowed to stir at room temperature overnight. The mixture was diluted with water (1200 ml), and extracted with toluene (2×400 ml). The toluene extract was washed with water, dried and concentrated to get 116.66 g., of a red oil. This was distilled at 1.2 mm, b.p. 125° C. to get a colorless oil, that solidified upon standing at room temperature, 104.32 g., (94 % yield). lit.[1] m.p. 29–30° C. Mass Spec: (mlz): 222, (M+).

EXAMPLE 16

2-Bromo-9,9-diethylfluorene

To a solution of diethylfluorene (22.2 g., 0.1 mol.) in propylene carbonate (100 ml), N-bromosuccinimide (17.8 g., 0.1 mol.) was added at 57° C. in portions and the mixture was stirred for 30 minutes at 60° C. The mixture was diluted with 1200 ml of water and extracted with 500 ml of toluene. The toluene extract was washed 3 times with 300 ml portions of water, dried and concentrated. The crude product from 3 batches of the same size totaled 117 g. of oil. This was distilled at 2 mm. The first fraction, b.p. 90–93° C., 22.33 g. was found to be propylene carbonate. The second fraction, b. p. 155–165° C., 81.0 g. (89.7% yield) was the desired product. Mass Spec: (m/z): 300, 302 (M+).

EXAMPLE 17

2-(9,9-Diethyl-2-fluorenyl)-benzothiazole

This compound has been prepared by three different methods:

Method A: To a solution of 2-bromo-9,9-diethyl fluorene, (45.0 g., 0.15 mol), in THF (270 ml), cooled in a dry ice-acetone bath, a solution of n-butyl lithium in hexanes (105 ml, 1.6M, 0.168 mol) was added over 20 minutes and the red solution was treated with a solution of DMF (20 ml, 0.2865 mol ) in THF (30 ml) after 30 minutes. The reaction mixture was removed from the cooling bath after 1.5 hours. When the temperature of the reaction mixture reached −5° C., it was treated with a mixture of conc. hydrochloric acid (15 ml) and water (60mi). The organic phase was washed with water, the aqueous phase was extracted with toluene, and the combined organic extracts were concentrated after drying to leave the crude aldehyde as a thick colorless oil, 41.95 g.

A mixture of the crude aldehyde from above, 2-aminothiophenol (17 ml., 0.155 mol) and DMSO (100 ml) was held at 195° C. for 1 hour, and poured into water. The separated colorless tar was dissolved in toluene (600 ml), the toluene solution was washed with water, dried and concentrated. The residual solids were recrystallized from toluene-heptane to get the benzothiazole in two crops, 29.84 g., m.p. 128–131° C. and 10.13 g., m.p. 135–135° C. Total yield was 75%. Mass. Spec: (m/z) 355 (M+). A sample for analysis was obtained by sublimation at 0.5mm. and at 130° C. Anal: Calcd for $C_{24}H_{21}NS$: C, 81.10; H, 5.96; N, 3.94 and S, 9.00. Found; C, 80.77; H, 6.07; N, 3.55 and S, 8.98.

Method B: To a mechanically stirred mixture of 9,9-diethylfluorene, (33.3 g., 0.15 mol), and a 1M solution of titanium(IV) chloride in dichloromethane (300mi, 0.3 mol), cooled to 0° C., a solution of dichloromethyl methyl ether (17ml, 21.6 g., 0.19 mol) was added, and the mixture was stirred for 18 hours, when the temperature was allowed to rise to 20° C. The reaction mixture was poured into a mixture of ice and water, the dichloromethane layer was washed with water, dried and concentrated to get an oil. Mass Spec: (m/z) 250 (M+). The crude aldehyde was reacted with 2-aminothiophenol, to get the benzothiazole, m.p. 137–139° C.; 15.75 g., (30% yield for the two steps). Starting with the same quantity of diethyl fluorene and using tin (IV) chloride as the catalyst in the formylation step, there was obtained 19.54 g., (37% yield), m.p. 136–138° C., of the desired benzothiazole.

Method C: To a solution of 2-bromo-9,9-diethyl fluorene, (45.0 g., 0.15 mol), in THF (270ml), cooled in a dry ice-acetone bath, a solution of n-butyl lithium in hexanes (105 ml, 1.6M, 0.168 mol) was added over 20 minutes and the red solution was treated with a solution of DMF (20 ml, 0.2865 mol) in THF (30 ml) after 30 minutes. The reaction mixture was removed from the cooling bath after 1.5 hours. When the temperature of the reaction mixture reached −5° C., it was treated with a mixture of conc. hydrochloric acid (15 ml) and water (60 ml). The organic phase was washed with water, the aqueous phase was extracted with toluene, and the combined organic extracts were concentrated after drying to leave the crude aldehyde as a thick colorless oil, 41.95 g.

A mixture of the crude aldehyde from above, 2-aminothiophenol (17 ml., 0.155 mol) and DMSO (100 ml) was held at 195° C. for 1 hour, and poured into water. The separated colorless tar was dissolved in toluene (600ml), the toluene solution was washed with water, dried and concentrated. The residual solid was recrystallized from toluene-heptaneto get the benzothiazole in two crops. 29.84 g., m.p. 128–131° C. and 10.13 g., m.p. 135–135° C. Total yield was 75%. Mass. Spec: (m/z) 355 (M+). A sample for analysis was obtained by sublimation at 0.5mm. and at 1300C. Anal. Calcd. for $C_{24}H_{21}NS$: C, 81.10; H, 5.96; N, 3.94; S, 9.00. Found: C, 80.77; H, 6.07; N, 3.55; S 8.98.

EXAMPLE 18

2-(9,9-Diethvl-7-nitro-fluoren-2-yl)benzothiazole

A mixture of diethylfluorenyl benzothiazole, (9.0 g.), acetic acid (75 ml), and conc. nitric acid (sp. gr. 1.42, 25 ml) was held at 105° C. for 2 hours, cooled and filtered. These solids were stirred in dilute sodium hydroxide solution and filtered to get 10 g. of crude solid. This was recrystallized from toluene-heptane to afford 7.58 g., 75% of the nitrobenzothiazole, m.p. 209–2140C. Mass Spec: (m/z) 400 (M+). Two recrystallizations from toluene-heptane raised the m.p. to 231.6–233.5° C. Anal. Calcd. for $C_{24}H_{20}N_2O_2S$: C, 71.98; H, 5.03; N, 7.00; S, 7.99. Found: C, 71.70, H, 4.90; N, 6.62; S, 7.77.

In other runs, there was isolated a small quantity of an isomer, m.p. 166–167° C. m/z 400 and a dinitro derivative was also detected by mass spectroscopy.

EXAMPLE 19

9,9-diethyl-7-(2-benzothiazolyl)-2-fluorenamine

A mixture of the nitrofluorenyl benzothiazole (5.0 9.), ammonium formate (7.0 g.), 10% Pd on carbon (0.5 g.) in DMF (50 ml) was stirred at room temperature for 18 hours, and at 60° C. for 3 hours. The solid that separated on dilution with water, was collected, dissolved in hot toluene (60m1), filtered, and the filtrate was concentrated to ca. 25–30mi. On the addition of heptane (20mi) to the concentrated solution, the product crystallized out as bright yellow solids, 3.99 g., (86% yield), m.p. 206–207° C. Mass Spec: (m/z) 370 (M+). Recrystallization from toluene-heptane raised the m.p. to 207–208° C. Anal. Calcd. for $C_{24}H_{22}N_2S$: C, 77.81; H, 5.98; N, 7.56; S, 8.64. Found: C 77.80; H, 6.12; N, 7.49; S, 8.63.

EXAMPLE 20

N,N N-Tris-(7-(2-benzothiazolyl)-9,9-diethyl-2-fluorenyl)amine

A mixture of 2-(2-benzothiazolyl)-9,9-diethyl-2-fluoreneamine, 19 (3.7 g., 10 mmol.), 7-iodo-9,9-diethyl-2-fluorenyl benzothiazole, 14 (14.43 g., 30 mmol), potassium carbonate, (14.0 g., 100 mmol), 18-crown-6 (0.6 g., 2.3 mmol), copper bronze, (2.0 g., 31.5 mmol) and 1,2-dichlorobenzene (50 ml), was held at 180–182° C. for 24 hours, cooled and filtered. The solids were washed with THF, and the combined filtrate was concentrated, and then adsorbed on to 100 g. of alumina. The product mixture supported on alumina, was transferred to a column of alumina (750 g.), and the column with heptane (1000 ml), 1:9 toluene-heptane (1500 ml), 1:3 toluene-heptane (2000 ml) 1 toluene-heptane (16000 ml). The product came out in 1:3 heptane-toluene eluates (10,000 ml). The product was isolated after recrystallization from toluene-ethanol (v/v, 1:1), 7.38 g., (69% yield), m.p. 302.8–307.8° C. Low resolution FAB mass spec: (m/z) 1077.4 (M+H)+. A sample for analysis was obtained by recrystallizations from toluene-heptane (1:1) and was dried at 150° C. for 5 hours at 0.4 mm. m.p. 306.5–308.9° C. Anal. Calcd. for $C_{72}H_{60}N_4S_3$: C, 80.27; H, 5.61; N, 5.20; S, 8.91. Found: C, 79.89; H, 5.56; N, 4.86; S, 8.64.

The two photon absorption coefficient (β) and the molecular two-photon cross-section ($\sigma_2$) were determined from an experimental measurement of the transmitted intensity of a laser beam at 800 nm as a function of the incident intensity. The data are presented in Table I, below.

TABLE I

| Chromophore (Example) | $\lambda_{max}$ (nm)* | β** | $\delta_2'$*** | $\delta_2'$/MW**** |
|---|---|---|---|---|
| 11 | 395 (479) | 4.7 | 97.5 | 19 |
| 12 | 413 (478) | 12.4 | 255.44 | 31.9 |
| 20 | 428 | — | 228.16 | 21.2 |
| 6 | 376.5 (485) | 5.1 | 105.2 | 17.5 |
| 9 | 386 (477) | 21.6 | 178.56 | 18.8 |

TABLE I-continued

| Chromophore (Example) | $\lambda_{max}$ (nm)* | β** | $\delta_2'$*** | $\delta_2'$/MW**** |
|---|---|---|---|---|
| 10 | 392 | | 33.5 | 238.08 | 18.2 |

*Linear Abs. (Emission; excited at 390 nm)
**cm/GW at 0.2 mol/L
***($\times 10^{-48}$ cm$^4$·sec ph · molecule)
****($\times 10^{-50}$ cm$^4$·sec·mole ph · molecule · g)

Having thus described exemplary embodiments of the present invention, it should be noted by those skilled in the art that the disclosures herein are exemplary only and that alternatives, adaptations and modifications may be made within the scope of the present invention.

We claim:
1. A chromophore of the formula:

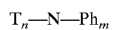

wherein Ph is a phenyl group, n has a value of 2 or 3 and m has a value of 3−n, and
wherein T is

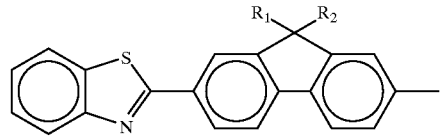

wherein $R_1$ and $R_2$ are alkyl groups having 1 to 20 carbon atoms.

2. The chromophore of claim 1 wherein n is 2, and $R_1$ and $R_2$ are ethyl groups.

3. The chromophore of claim 1 wherein n is 3, and $R_1$ and $R_2$ are ethyl groups.

4. A chromophore of the formula:

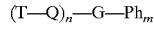

wherein T is

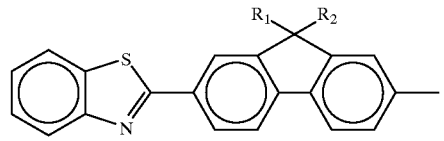

wherein $R_1$ and $R_2$ are alkyl groups having 1 to 20 carbon atoms, and wherein Q is a single bond or 1,4-phenylene, Ph is a phenyl group, n has a value of 1–4 and m has a value of 4−n, and wherein G is a core unit selected from the group consisting of

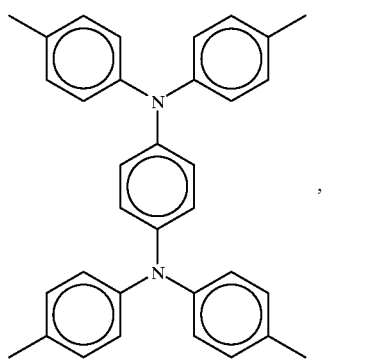
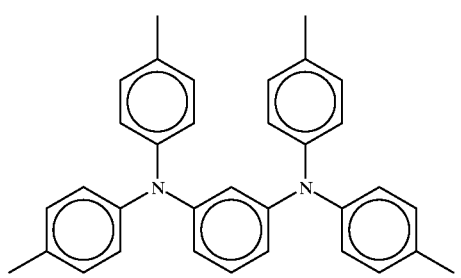
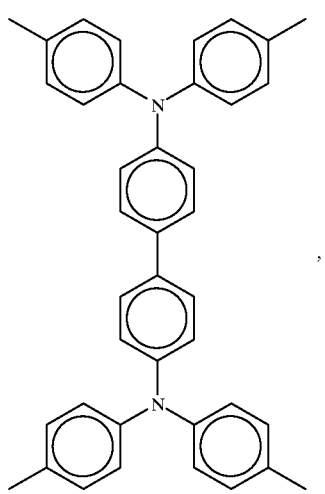
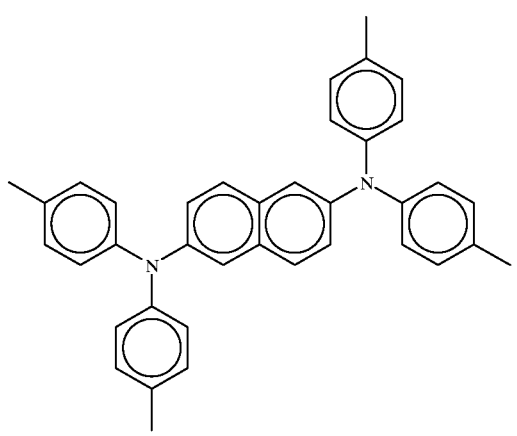
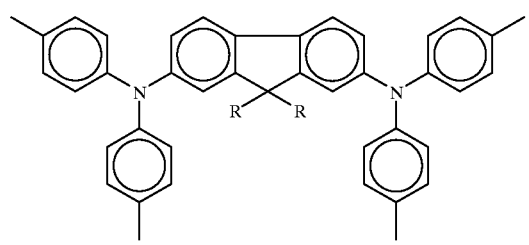
and
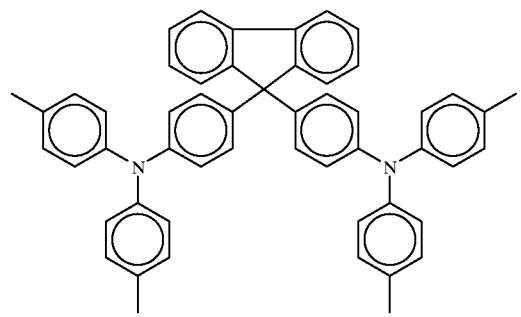
5. A chromophore of the formula:
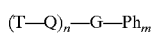
wherein T is
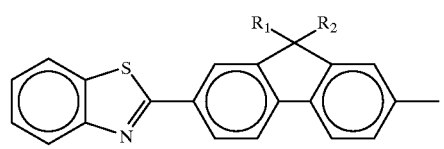
wherein $R_1$ and $R_2$ are alkyl groups having 1 to 20 carbon atoms, and wherein Q is a single bond or 1,4-phenylene, Ph is a phenyl group, n has a value of 1–6 and m has a value of 6–n, and wherein G is a core unit having the structure
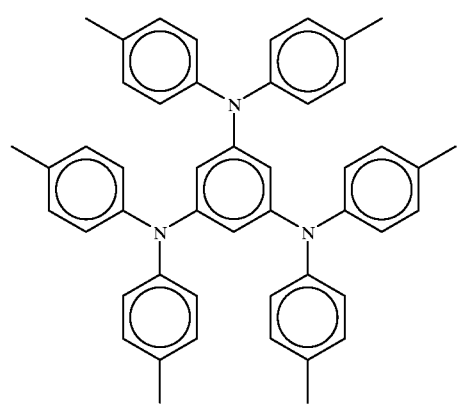
6. A chromophore of the formula:

(T—Q)₂—N—Ph
wherein Q is 1,4-phenylene, Ph is a phenyl group, and T is
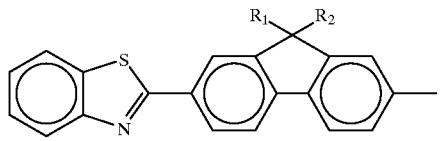
wherein R₁ and R₂ are alkyl groups having 1 to 20 carbon atoms.
7. The chromophore of claim 6 wherein R₁ and R₂ are ethyl groups.
8. A chromophore of the formula:
(T—Q)₃—N
wherein Q is 1,4-phenylene and T is
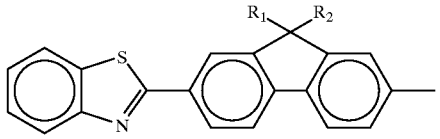
wherein R₁ and R₂ are alkyl groups having 1 to 20 carbon atoms.
9. The chromophore of claim 8 wherein R₁ and R₂ are ethyl groups.
* * * * *